US012797464B2

(12) United States Patent
Xue et al.

(10) Patent No.: US 12,797,464 B2
(45) Date of Patent: Nov. 17, 2026

(54) METHOD FOR PREPARING COMBINATION VACCINE ADJUVANT BASED ON CARBOXYL MODIFIED ALUMINUM OXYHYDROXIDE NANOPARTICLES

(71) Applicant: DALIAN UNIVERSITY OF TECHNOLOGY, Dalian (CN)

(72) Inventors: Changying Xue, Dalian (CN); Bingbing Sun, Dalian (CN); Hang Bao, Dalian (CN); Zhihui Liang, Dalian (CN)

(73) Assignee: DALIAN UNIVERSITY OF TECHNOLOGY, Dalian (CN)

( * ) Notice: Subject to any disclaimer, the term of this patent is extended or adjusted under 35 U.S.C. 154(b) by 842 days.

(21) Appl. No.: 18/002,822

(22) PCT Filed: Dec. 20, 2021

(86) PCT No.: PCT/CN2021/139666

§ 371 (c)(1),
(2) Date: Dec. 21, 2022

(87) PCT Pub. No.: WO2022/242162

PCT Pub. Date: Nov. 24, 2022

(65) Prior Publication Data

US 2023/0241209 A1 Aug. 3, 2023

(30) Foreign Application Priority Data

May 21, 2021 (CN) ........................ 202110558430.5

(51) Int. Cl.
*A61K 39/39* (2006.01)
*A61K 39/00* (2006.01)

(52) U.S. Cl.
CPC .... *A61K 39/39* (2013.01); *A61K 2039/55505* (2013.01)

(58) Field of Classification Search
CPC .......... A61K 39/39; A61K 2039/55505; A61K 2039/55555; A61K 2039/55561; A61K 2039/572; A61K 2039/575; A61K 39/12; A61K 2039/54; A61P 31/14; C12N 2770/20034
See application file for complete search history.

(56) References Cited

U.S. PATENT DOCUMENTS

| | | | |
|---|---|---|---|
| 2011/0123632 | A1 | 5/2011 | Kaye et al. |
| 2016/0144023 | A1 | 5/2016 | Cui et al. |

FOREIGN PATENT DOCUMENTS

| | | | | | |
|---|---|---|---|---|---|
| CN | 103140239 | A | | 6/2013 | |
| CN | 110588015 | A | | 12/2019 | |
| CN | 111643662 | A | | 9/2020 | |
| CN | 111658617 | A | | 9/2020 | |
| CN | 113274492 | A | | 8/2021 | |
| WO | WO1993007883 | A1 | * | 4/1993 | |
| WO | WO-2021229014 | A1 | * | 11/2021 | .......... A61K 39/385 |

OTHER PUBLICATIONS

Bartczak D, Kanaras AG. Preparation of peptide-functionalized gold nanoparticles using one pot EDC/sulfo-NHS coupling. Langmuir. Aug. 16, 2011;27(16):10119-23 (Year: 2011).*

CytoDiagnostics, âGeneral Protocol for Coupling Biomolecules to Carboxylate Particles Using EDC/Sulfo-NHS.â Echo BioSystems, Sep. 22, 2020 (Year: 2020).*

Meder et al. Protein adsorption on colloidal alumina particles functionalized with amino, carboxyl, sulfonate and phosphate groups. Acta Biomater. Mar. 2012;8(3):1221-9 (Year: 2012).*

Sun et al. Enhanced Immune Adjuvant Activity of Aluminum Oxyhydroxide Nanorods through Cationic Surface Functionalization. ACS Appl Mater Interfaces. Jul. 5, 2017;9(26):21697-21705 (Year: 2017).*

Tian et al. The novel complex combination of alum, CpG ODN and HH2 as adjuvant in cancer vaccine effectively suppresses tumor growth in vivo. Oncotarget. Jul. 11, 2017;8(28):45951-45964 (Year: 2017).*

Greg T. Hermanson, Chapter 14—Microparticles and Nanoparticles, Editor(s): Greg T. Hermanson, Bioconjugate Techniques (Third Edition), Academic Press, 2013, pp. 549-587 (Year: 2013).*

Wei et al. Polyvalent Immunostimulatory Nanoagents with Self-Assembled CpG Oligonucleotide-Conjugated Gold Nanoparticles, Angew. Chem. Int. Ed. 2012, 51, 1202-1206 (Year: 2012).*

* cited by examiner

*Primary Examiner* — Joanne Hama
*Assistant Examiner* — Emmanuel Led Yotchom Pendie
(74) *Attorney, Agent, or Firm* — NKL Law; Allen Xue

(57) ABSTRACT

A method for preparing a combination adjuvant is based on carboxyl modified aluminum oxyhydroxide nanoparticles. The preparation method uses carboxylated hydroxyl oxide nanoparticles as a carrier, but is not limited to the role of a carrier. The carboxylated hydroxyl oxide nanoparticles are combined with a novel CpG-ODN adjuvant, such that the half-life period of a CpG adjuvant is prolonged. The combination of adjuvants shows a synergistic effect, such that the Th2 type immune stimulation ability is enhanced, and the possibility of Th1 type immunity is also given to the adjuvant.

10 Claims, 10 Drawing Sheets

METHOD FOR PREPARING COMBINATION VACCINE ADJUVANT BASED ON CARBOXYL MODIFIED ALUMINUM OXYHYDROXIDE NANOPARTICLES

TECHNICAL FIELD

The present disclosure relates to the technical field of biomedical technology, in particular to a method for preparing a combination vaccine adjuvant system based on carboxyl modified aluminum oxyhydroxide nanoparticles, and the application thereof for immunotherapy and prevention in vivo and in vitro.

BACKGROUND

Infectious diseases are a kind of diseases widely prevalent among people, between people and animals, or among animals. Its symptoms are serious and easy to spread among bodies, and are difficult to treat and have a long-term treatment cycle. Infectious diseases greatly threaten human life and health and even cause social panic, which are one of the main causes of human death. For example, the COVID-19 that broke out at the end of 2019 has greatly affected human normal life. Antibiotic therapy, as a commonly used method for treatment of infectious diseases, can play an effective role in treatment, but excessive antibiotics also brings great damage to human organs and nerves, and drug resistance will make infectious diseases more stubborn. However, vaccination is one of the most effective measures to reduce the mortality of infectious diseases, can even contain the spread of infectious diseases at the root. Vaccination has become a powerful tool for the treatment of a variety of infectious diseases so far.

The vaccine adjuvant involved in the present invention, also known as immunomodulator or immunopotentiator, as an additive of vaccine, can enhance immune response of the body to the antigen or even change the type of immune response by means of being injected into bodies before or at the same time with the antigen. So far, many vaccine adjuvants have been approved by FDA for use in human vaccines. Among them, the CpG-ODN adjuvant refers to oligodeoxynucleotides containing non-methylated cytosine guanosine motif (CpG). The oligodeoxynucleotides can be specifically recognized and internalized into endosome niosomes containing Toll-like receptor 9 to promote the expression secretion of proinflammatory factor. As an adjuvant, CpG-ODN adjuvant can induce antigen presenting cells to activate and mature to promote TH1 immune response. However, due to the particularity of nucleic acid structure, it will be inactivated by rapid enzymolysis in vivo, which limits its immune adjuvant effect. By the modification of skeleton phosphorothioate of the CpG-ODN adjuvant, the half-life of free CpG can be increased and the immune response can be improved, but it also results in the reduction of specific binding. In recent years, studies have found that if CpG-ODN is co-delivered with protein antigens or tiny particles, the enzymolysis will be reduced and the adjuvant effect will be stronger. However, the safety of the composite particle carriers and the influence of the composite modes on the adjuvant effect have been limiting its development. Therefore, it is still necessary to further study on the composite particles types and combination modes in this field to prepare safer and more efficient combination vaccine adjuvants.

As the first adjuvant approved by the FDA for human vaccine, aluminum adjuvant mainly promotes Th2 immune response, having good safety and widely used. Therefore, the present disclosure uses the aluminum salt adjuvant mainly of Th2 type as carrier, after carboxyl modification, it is co-delivered with amino modified CpG-ODN to prepare a combination vaccine adjuvant, which is expected to enhance the efficacy of adjuvant, so as to provide a theoretical basis for the development and design of engineering vaccine adjuvant.

SUMMARY OF THE INVENTION

In view of the above basis, it's an object of the present disclosure to provide a method for preparing a combination vaccine adjuvant based on carboxyl modified aluminum oxyhydroxide nanoparticles, the prepared combination vaccine adjuvant particles, and a method for verifying the effect of adjuvant.

On the one hand, the present disclosure provides a method for preparing a combination vaccine adjuvant based on carboxyl modified aluminum oxyhydroxide nanoparticles. By carboxyl surface modification of aluminum oxyhydroxide and bonding with amino-terminated CpG-ODN, a combination vaccine adjuvant is obtained.

On the other hand, the present disclosure explores the safety of the combination vaccine adjuvant in immune system and influence on the immune effect.

The present disclosure provides a method for preparing a combination adjuvant based on carboxyl modified aluminum oxyhydroxide nanoparticles, including the following steps of:

S1. Carboxyl modification of aluminum oxyhydroxide nanoparticles: dispersing aluminum oxyhydroxide nanoparticles in deionized water or ethanol to obtain a hydroxyl aluminum nanoparticle suspension, adding a silane coupling agent having carboxyl groups or anhydrides to react. As a precursor, the silane coupling agent having carboxyl groups or anhydrides is used for surface modification of the aluminum oxyhydroxide nanoparticles. The precursor and the aluminum oxyhydroxide nanoparticles are stirred to full react, after washing and drying, the carboxyl modified aluminum oxyhydroxide nanoparticles are obtained.

S2. Dispersing the carboxyl modified aluminum oxyhydroxide nanoparticles in a buffer to obtain a carboxylated aluminum oxyhydroxide nanoparticle suspension, adding 1-(3-dimethyl aminopropyl)-3-ethylcarbodiimide hydrochloride (EDC) and N-hydroxysulfosuccinimide (sulfo-NHS) to react with stirring, so as to activate the product of Step S1 (carboxyl modified aluminum oxyhydroxide nanoparticles), to obtain carboxylated aluminum oxyhydroxide nanoparticles, and then adding CpG (CpG-ODN), the carboxylated aluminum oxyhydroxide nanoparticles fully reacting with the amino-terminated CpG-ODN to obtain a final combination adjuvant product after washing.

Preferably, in step S1, the silane coupling agent is dissolved in deionized water or ethanol to prepare a precursor solution. The precursor solution is treated by ultrasound for a certain time, and then the aluminum oxyhydroxide nanoparticle suspension is added for reaction with stirring.

For the above technical solution, preferably, in step S1, the aluminum oxyhydroxide nanoparticles are aluminum nanoparticles having hydroxyl groups on surface or hydroxyl modified aluminum nanoparticles.

For the above technical solution, preferably, in step S1, the silane coupling agent having carboxyl groups or anhydrides is 3-(triethoxylmethylsilyl) propylsuccinic anhydride.

For the above technical solution, in step S1, a concentration of the aluminum oxyhydroxide nanoparticle suspension is 0.1 to 20 mg/mL, and preferably 1 mg/mL; a volume ratio of the silane coupling agent to the aluminum oxyhydroxide nanoparticle suspension is 0.01 to 1:100 (V/V), and preferably 0.01:100 (V/V).

For the above technical solution, preferably, in step S1, the stirring speed is 300 to 1000 rpm, and the conditions of the reaction are of firstly reacting with stirring at 25 to 35° C. for 30 to 60 minutes, and then reacting with stirring at 100 to 150° C. for 60 to 200 minutes.

For the above technical solution, in step S2, pH value of the buffer is less than or equal to 7, and preferably 4 to 5; and preferably, sulfo-NHS and EDC are added at the same time, and the buffer is MES buffer.

For the above technical solution, in step S2, a concentration of the 1-(3-dimethyl aminopropyl)-3-ethylcarbodiimide hydrochloride and N-hydroxythiosuccimide is greater than or equal to 100 M, and preferably greater than or equal to 200 M, that is, excess to ensure full activation; a concentration of the carboxylated aluminum oxyhydroxide nanoparticle suspension is 0.1 to 20 mg/mL, and preferably 5 mg/L; and a mass ratio of the carboxylated aluminum nanoparticles to CpG is 5 to 100:1, and preferably 50:1.

For the above technical solution, preferably, in step S2, the carboxyl-activated aluminum oxyhydroxide nanoparticles are reacted with 5' end or 3' end of amino-terminated CpG motifs to obtain a combination vaccine adjuvant of 3'-CpG-free or 5'-CpG-free. The carboxyl-activated aluminum oxyhydroxide nanoparticles conduct a coupling reaction with 5' amino-terminated CpG to obtain a 3'-CpG-free combination vaccine adjuvant, and the carboxyl-activated aluminum oxyhydroxide nanoparticles conduct a coupling reaction with 5'3' amino-terminated CpG to obtain a 5'-CpG-free combination vaccine adjuvant.

For the above technical solution, preferably, in step S2, CpG-ODN, as an agonist of cellular immunity Toll-like receptor 9, has strong specificity. The effects of different CPG-ODN motifs in different animals are very different, for example, CpG-ODN (ODN1826) has strong specificity for mice and CpG-ODN (ODN2006) has strong specificity for humans. The present disclosure is suitable for the above CPG-ODN but not limited.

For the above technical solution, preferably, in step S2, the stirring speed of the activation reaction is 500 to 1000 rpm, the activation time is 20 to 40 minutes, and the activation reaction is carried out at room temperature (generally 25° C.).

For the above technical solution, preferably, in step S2, the reaction temperature is 25 to 37° C., and the reaction time is 2.5 to 5 hours.

On another hand, the present disclosure also provides a combination vaccine adjuvant prepared by the above method for immunotherapy and prevention in vitro and in vivo.

On another hand, the present disclosure also provides an application of the combination vaccine adjuvant in vaccine production, wherein the vaccine is a subunit vaccine or an inactivated vaccine, such as COVID-19 vaccines etc., and the vaccine preparation is used for intramuscular injection. The immune procedure is two immunizations in which the adjuvant and the antigen are successively injected at the same site.

In addition, the present disclosure also discloses a method for exploring immune effect of the combination vaccine adjuvant in the immune system. The method includes but is not limited to technologies of combination adjuvant toxicity, immune cytokine level analysis and immune effect exploration in vivo, including the following methods:

1) Combination adjuvant toxicity and immune inflammatory level: after stimulation of dendritic cells and mononuclear macrophages of mice or humans by a series of combination adjuvant materials for a certain time, viability of the existing cells is detected by MTS method and toxicity of the materials to cells is reflected by measuring the light absorption at a specific wavelength; and enzyme-linked immunosorbent assay (ELISA) is used to detect the immune inflammation level and immune cytokines level.
2) Recruitment and activation of immune cells in vivo: after stimulation with materials for a certain time by mouse intraperitoneal injection model, PBS buffer is used to lavage and peritoneal lavage fluid is collected; the recruitment of immune cells in the peritoneal lavage fluid is investigated by flow cytometry, and the secretion of immune cytokines in the peritoneal is detected by enzyme-linked immunosorbent assay (ELISA).
3) Long-acting immune effect: by using mouse intramuscular injection model, the receptor-binding domain subunit (RBD) of novel coronavirus inactivated S protein is used as an antigen, after immunization, the serum of mice is collected and the specific antibody level in serum is detected by enzyme-linked immunosorbent assay (ELISA).

For the above technical solution, in step 1), the stimulation time is 16 hours or longer, and the MTS treatment time is preferably 50 minutes.

For the above technical solution, preferably, in step 2), the stimulation time after injection of materials is 6 to 48 hours, and the control group can be normal saline, PBS buffer or other physiological activity simulation solution.

For the above technical solution, in step 3), two immunizations are required. The first immunization is preferably on day 0 and the booster immunization is preferably on day 21. The booster immunization is helpful to provide more significant effects.

The advantages and positive effects of the present disclosure:

Carboxylated hydroxyl oxide nanoparticles are used as a carrier (but is not limited to the carrier effect) to combine with the new-type adjuvant of CpG-ODN to prolong the half-life of CpG adjuvant. The method of carboxylation is simple and convenient to operate. The combination of adjuvant shows a synergistic effect, which not only enhances its Th2 immune stimulation ability, but also gives it the possibility of Th1 immunity. The present disclosure also provides a variety of cell models and animal models to comprehensively evaluate the combination adjuvant. In addition, the adjuvant effect verification process of the present disclosure is simple, easy to control and short in time, providing a good idea for the engineering development and utilization of vaccine adjuvants.

DETAILED DESCRIPTION OF DRAWINGS

FIG. 1 shows the transmission electron microscope characterization results of aluminum oxy oxyhydroxide nanorods before and after carboxylation and combination, in which are successively the original aluminum oxyhydroxide nanorods (denoted as AlOOH), carboxylated aluminum oxyhydroxide nanorods (denoted as Al—COOH), and the combination adjuvants of aluminum oxyhydroxide combined with CpG having different ends (denoted as 3'-CpG-free and 5'-CpG-free), and the scale bar in the figure is 200 nm.

(FIG. 3A represents THP-1 cell line and FIG. 3B represents BMDC cell line).

FIG. 7A represents the titer level of total IgG antibody and FIG. 7B represents the titer level of $IgG_{2a}$ antibody.

FIG. 8A represents the statistic of the cell spots secreting IFN-γ and FIG. 8B represents the statistic of the cell spots secreting IL-4.

DETAILED DESCRIPTION OF PREFERRED EMBODIMENTS

The present disclosure is further described in detail below in conjunction with embodiments so that those ordinary skilled in the art may understand the present disclosure more comprehensively, but the implementations of the present disclosure are not limited to the embodiments.

The preparation method of aluminum oxyhydroxide nanoparticles (AlOOH) in the following embodiments is in reference to the Chinese Patent Application No. 201811297419.2.

Embodiment 1

Figure 1:
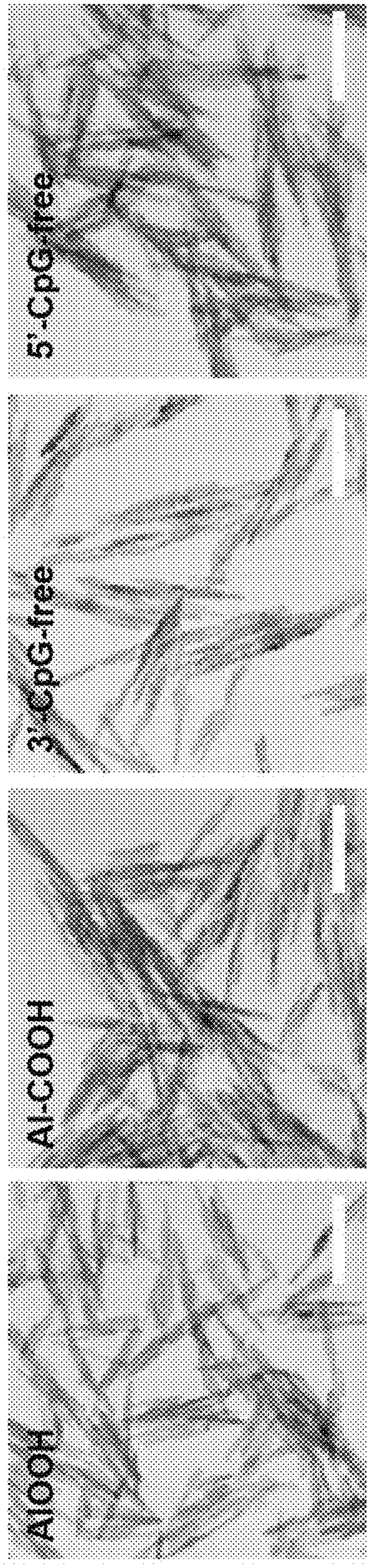
Figure 2:
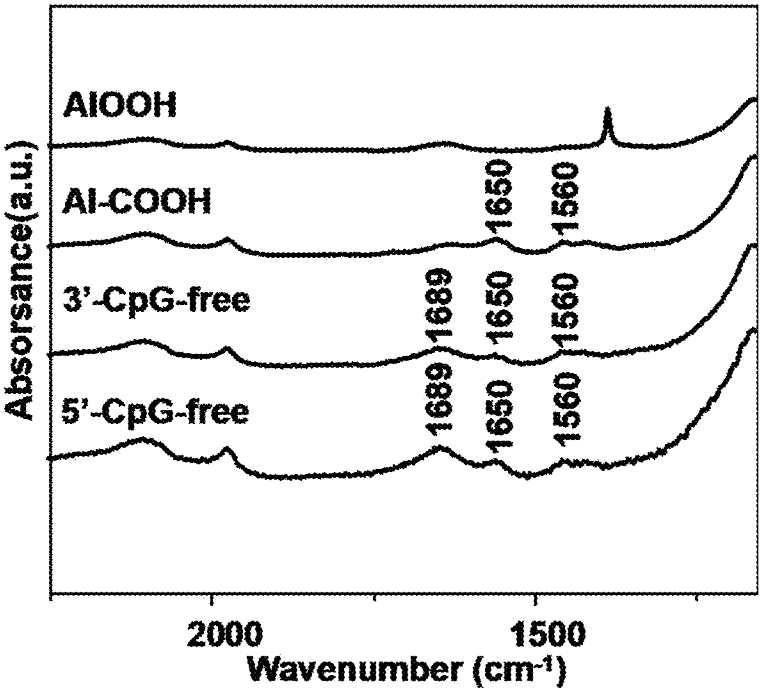
FIG. 2 shows the Fourier infrared characterization diagram of aluminum oxyhydroxide nanorods before and after carboxylation and combination.

This embodiment describes a method for surface carboxyl modification of aluminum oxyhydroxide, including the following steps that:

20 mg of aluminum oxyhydroxide nanoparticles (with hydrodynamic size of about 300 nm and zeta potential of about 40 mV) were dispersed in 10 mL of deionized water and were evenly dispersed by ultrasonic to obtain a nanoparticle suspension; 20 μL of 3-(triethoxylmethylsilyl)propylsuccinic anhydride was dissolved in 10 mL of deionized water and was treated by ultrasonic for 5 minutes to obtain a solution, after full dispersion, the solution was added into the nanoparticle suspension for reaction with stirring at a rotate speed of 600 rpm for 30 minutes at 25° C. and then for 90 minutes at 120° C., and a mixed solution was obtained. The mixed solution was fully washed by centrifugation with deionized water, and was dried at 60° C. to obtain a final carboxylated product (AL-COOH). The morphologies of aluminum oxyhydroxide nanoparticles before and after carboxylation were characterized by transmission electron microscope. As shown in FIG. 1, the carboxylation does not change the morphology characteristics of nanoparticles. The main functional groups of aluminum oxyhydroxide nanoparticles before and after carboxylation were characterized by Fourier transform infrared spectroscopy. As shown in FIG. 2, the carbon-oxygen double-bond absorption peak appears after carboxylation. The hydrodynamic size and Zeta potential were characterized by nanoparticle size analyzer. As shown in Table 1, the surface charge becomes significantly negative due to the introduction of carboxyl groups.

Embodiment 2

This embodiment describes a method for preparing a combination adjuvant of carboxylated aluminum oxyhydroxide and CpG-ODN, including the following steps that:

The product Al—COOH obtained in Embodiment 1 was suspended in 1 mL of MES buffer with pH 5 to prepare a 5 mg/mL of nanoparticle suspension. 19.2 mg of EDC and 21.7 mg of sulfo-NHS were dissolved in 500 μL of MES buffer with pH 5.0 respectively and successively transferred to the nanoparticle suspension, and conducted an activation reaction at a rotate speed of 600 rpm for 30 minutes at room temperature. After reaction, the solution was washed by centrifugation at 10000 rpm, and then was resuspended in 1 mL of MES buffer with pH 5.0, followed by adding 30 μL of CpG-ODN solution with a mass concentration of 0.67 mg/mL and ultra-pure water as solvent (CpG-ODN was purchased from Sangon Biotech) and reacting at room temperature for 3 hours. After reaction, the mixed solution was washed by centrifugation at 10000 rpm and resuspended in 5 mL of deionized water to obtain the combination vaccine adjuvant. The combination adjuvant obtained by combining with 5' amino-terminated CpG was denoted as 3'-CpG-free and the combination adjuvant obtained by combining with 3' amino-terminated CpG was denoted as 5'-CpG-free. The morphology of the combination nanoparticles was characterized by transmission electron microscope. It can be seen from FIG. 1 that the combination at chemical level does not change the material morphology characteristics. The main functional groups of the combination aluminum nanoparticles were characterized by Fourier transform infrared spectroscopy. It can be seen from FIG. 2 that there is amide bonds after combination. The hydrodynamic size and Zeta potential were characterized by the nanoparticle size analyzer. It can be seen from Table 1 that the surface charge becomes significantly negative and the particle size does not change significantly.

TABLE 1

Characterization results of hydrodynamic size and Zeta potential of aluminum oxyhydroxide nanorods before and after carboxylation and combination

| Sample | Zeta potential in water (mV) | Hydrodynamic size in water (nm) | Polydispersity |
|---|---|---|---|
| AlOOH | 40 | 317 ± 4 | 0.25 |
| Al—COOH | −20 | 368 ± 30 | 0.26 |
| 3'-CpG-free | −26 | 255 ± 2 | 0.17 |
| 5'-CpG-free | −29 | 221 ± 1 | 0.13 |

Embodiment 3

This embodiment provides a method for evaluating the toxicity of vaccine adjuvants.

Figure 3A:
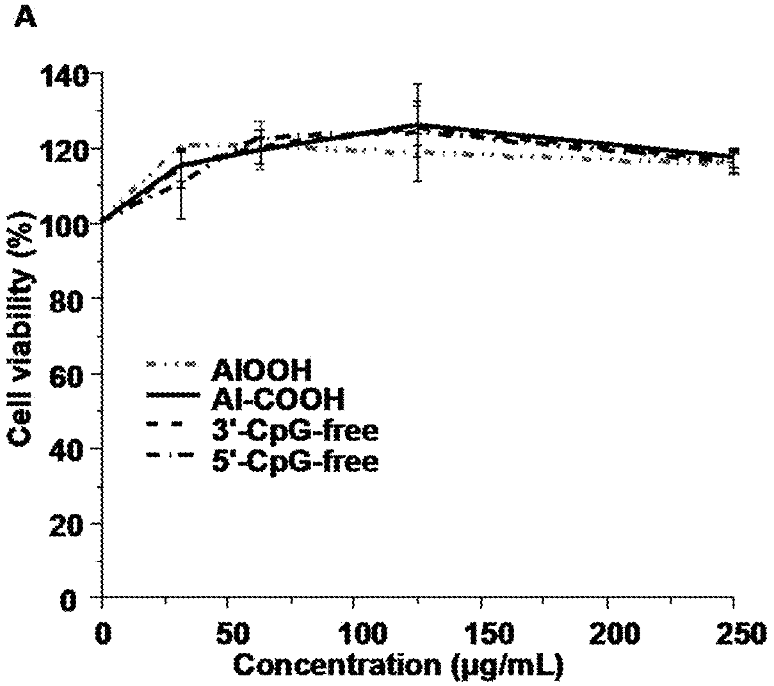
FIGS. 3A-3B show the effects of aluminum oxyhydroxide nanorods on viability of different cell lines before and after carboxylation and combination

THP-1 cells were inoculated in a 96-well plate with 30000 cells per well in advance, and the well plate was suspended in 100 μL of RPMI 1640 (Corning) complete medium. When inoculating, a multi-channel pipette was used to ensure that the number of cells per well is uniform. After incubation at 37° C. in a $CO_2$ constant temperature incubator for 16 hours, four groups of materials (respectively, aluminum oxyhydroxide nanoparticles (AlOOH), carboxylated nanoparticles (Al—COOH) obtained in Embodiment 1, and combination nanoparticles (3'-CpG-free and 5'-CpG-free) obtained in Embodiment 2) were diluted with the RPMI 1640 complete medium to 250 μg/mL, 125 μg/mL, 62.5 μg/mL and 31.25 μg/mL. The solution of the above well plate was replaced with the prepared materials to continue culture. Besides, a blank control group was set (Ctrl, without the above four materials but the same amount of medium). After culturing for 24 hours, the supernatant was removed, and the cells at bottom were incubated with 100 μL of RPMI 1640 complete medium containing 20% of MTS solution (purchased from Promega). After 40 minutes, the incubated supernatant was collected to measure the OD490. Compared with the blank group, cell viability ratio was obtained as shown in FIG. 3A. It can be seen from FIG. 3A that the cell viabilities are around 100%, indicating that the materials are safe and non-toxic.

Embodiment 4

This embodiment provides a method for evaluating the toxicity and immune inflammatory level of vaccine adjuvants.

Figure 4:
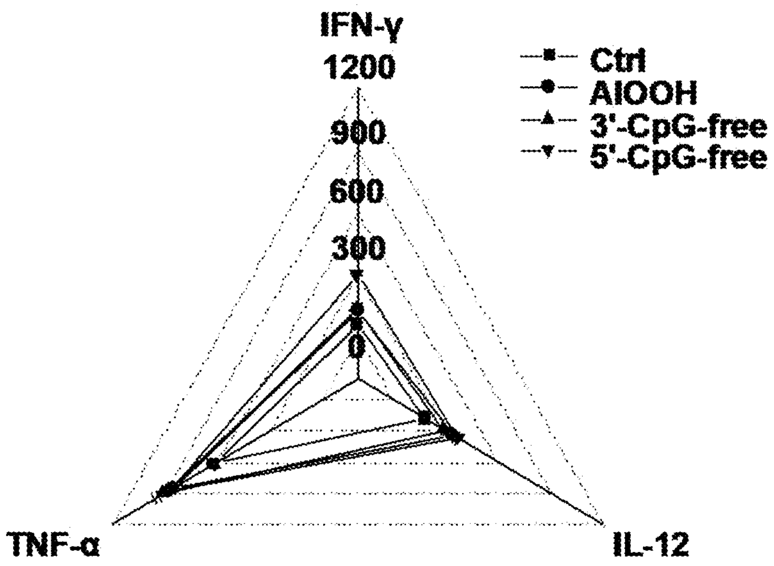
FIG. 4 shows the effect of aluminum oxyhydroxide nanorods on proinflammatory factor level in vitro before and after carboxylation and combination.

BMDC cells were inoculated in a 96-well plate with 30000 cells per well in advance, and the well plate was suspended in 100 μL of RPMI 1640 (Corning) complete medium. When inoculating, a multi-channel pipette was used to ensure that the number of cells per well is uniform. After incubation at 37° C. in a $CO_2$ constant temperature incubator for 16 hours, four groups of materials (respectively, hydroxyl alumina nanoparticles (AlOOH), carboxylated nanoparticles (Al—COOH) obtained in Embodiment 1, and combination nanoparticles (3'-CpG-free and 5'-CpG-free) obtained in Embodiment 2) were diluted with the RPMI 1640 complete medium to 250 μg/mL, 125 μg/mL, 62.5 μg/mL and 31.25 μg/mL. The solution of the above well plate was replaced with the prepared materials to continue culture. Besides, a blank control group was set (Ctrl, without the above four materials but the same amount of medium). After culturing for 24 hours, the supernatant of the above 96 well-plate was collected, and then the cytokine secretion level was measured by ELISA method to explore its immune activation effect. FIG. 4 shows cytokine secretion levels of IFN-7, IL-12, and TNF-α, respectively. In FIG. 4, the IFN-γ secretion shows that the combination adjuvant groups have obvious Th1 polarization and the 5'-CpG-free group has a better effect, indicating that the combination adjuvant not only enhances the Th2 type immune stimulation ability (IL-12, TNF-α), but also has the possibility of Th1 type (IFN-γ) immunity.

Figure 3B:
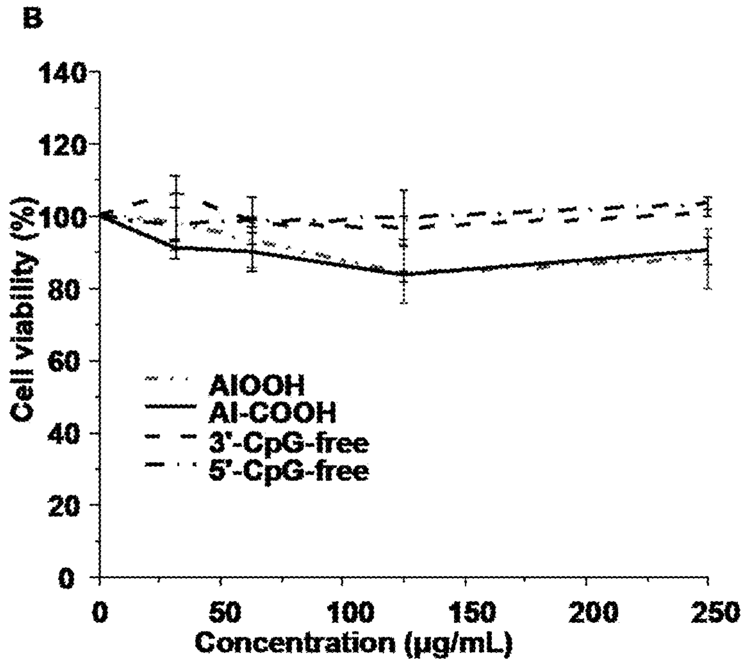

The cells at bottom of the well plate were incubated with 100 μL of RPMI 1640 complete medium containing 20% of MTS solution (purchased from Promega). After 40 minutes, the incubated supernatant was collected to measure the OD490. Compared with the blank group, cell viability ratio was obtained as shown in FIG. 3B. It can be seen from FIG. 3B that the cell viabilities are all greater than or equal to 80%, indicating that the material is almost non-toxic.

Embodiment 5

This embodiment provides a mouse intraperitoneal injection model and implementation method for evaluating the immune effect of vaccine adjuvant in vivo.

Figure 5:
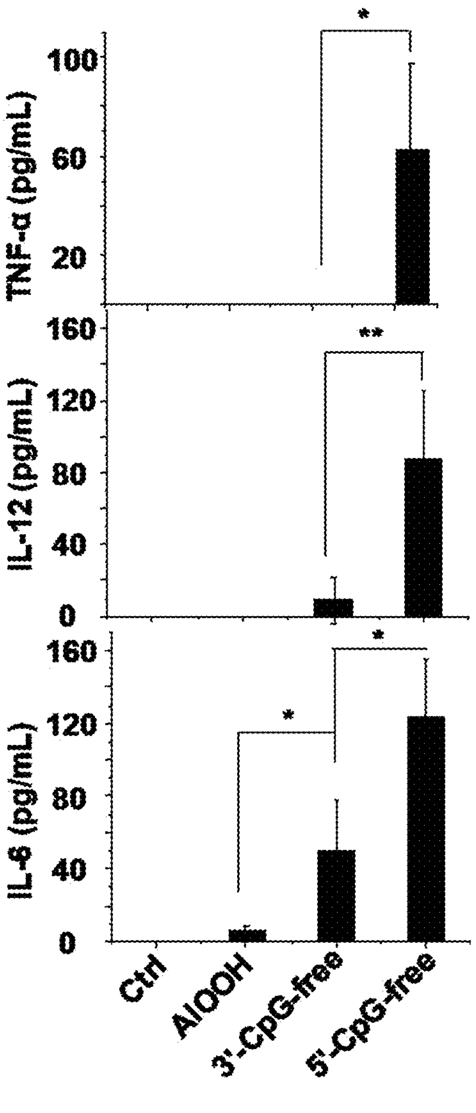
FIG. 5 shows the effect of aluminum oxyhydroxide nanorods on immune cytokines level in peritoneal fluid in vivo before and after carboxylation and combination.

1 mg/mL of solutions (PBS) of AlOOH, and 3'-CpG-free adjuvant and 5'-CpG-free adjuvant obtained in Embodiment 2 were prepared respectively. The prepared solution was injected into mouse enterocoelia in a dose of 50 μl per mouse, and a control group was set (Ctrl, only the same amount of normal saline was injected). After 6 hours, the peritoneal fluid was flushed with PBS and collected. The collected fluid was centrifuged at 4° C. and 1000 rpm for 6 minutes, and the supernatant was collected to explore the immune cytokine level by ELISA method. FIG. 5 shows cytokine levels of TNF-α, IL-6, and IL-12, respectively, indicating that the cytokine secretion levels in the combination adjuvant groups are significantly increased, and 5'-CpG-free group has a better effect.

Figure 6:
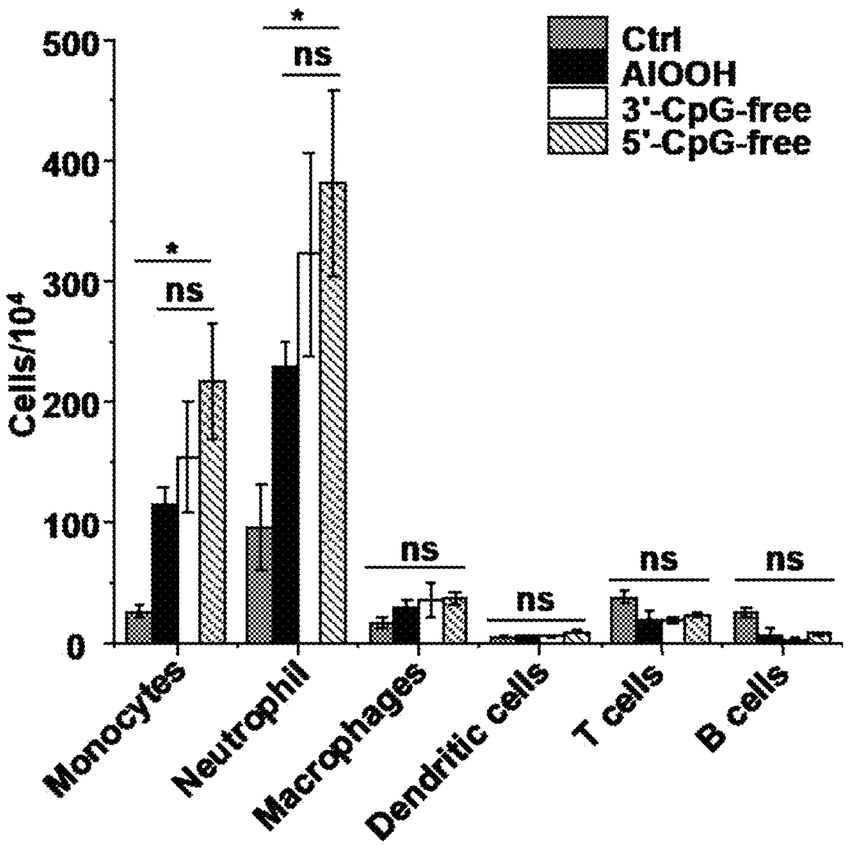
FIG. 6 shows the effect of aluminum oxyhydroxide nanorods on recruitment of peritoneal immune cells in vivo before and after carboxylation and combination.

The remaining cells after centrifugation were treated with red blood cell lysate to remove interfering red blood cells, followed by centrifuging the treated cells at 4° C. and 1000 rpm for 6 minutes and fully washing. Further, the cells were labeled with the following antibodies: monocytes ($SSC^{low/}{}_{med}CD11b^{+}Ly6c^{+}$), neutrophils ($SSChighCD11b^{+}Ly6c^{+}$), macrophages ($F4/80^{+}$), dendritic cells ($CD11c^{+}MHCII$), T cells ($CD45^{+}CD3^{+}$) and B cells ($CD45RB220^{+}$). After label treatment in dark for 30 minutes and washing with PBS, the cells were used for flow cytometric analysis. As shown in FIG. 6, the combination adjuvant groups, especially the 5'-cpg-free group, are beneficial to the recruitment of more immune cells.

Embodiment 6

This embodiment provides a mouse intramuscular injection model and implementation method for evaluating the long-acting immune effect of vaccine adjuvant in vivo.

Figure 7A:
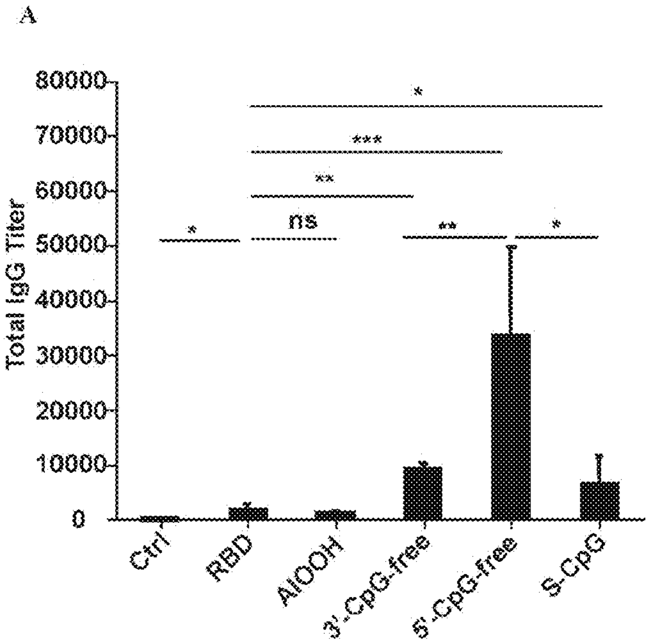
FIGS. 7A-7B show the effect of aluminum oxyhydroxide nanorods on titer of long-acting immune antibody in mice before and after carboxylation and combination. (A
Figure 7B:
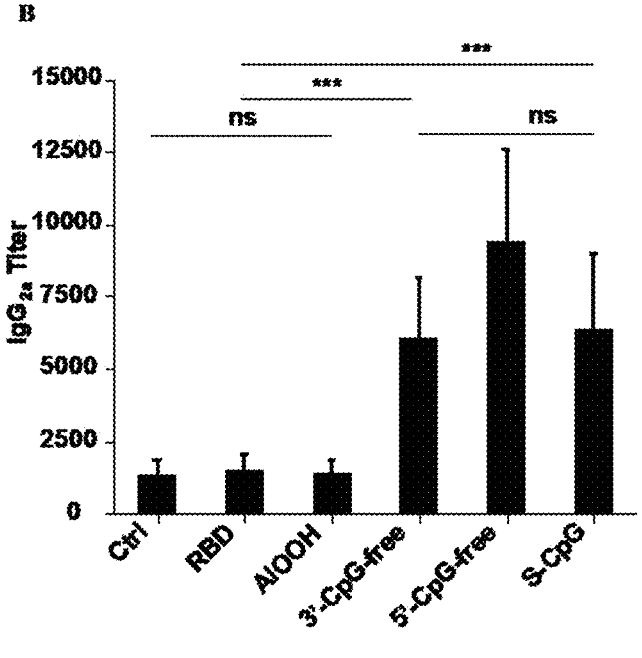

5 mg/mL of solutions (PBS) of AlOOH, and 3'-Cpg-free adjuvant and 5'-Cpg-free adjuvant obtained in Embodiment 2, and 60 μg/mL of novel coronavirus RBD antigen were respectively prepared. The prepared solution was intramuscularly injected into mouse in a dose of 50 μL per mouse. The mouse was subjected to first immunization and booster immunization respectively according to the immunization procedure of Day 0 and Day 21. Serum and spleen of the mouse were collected after 21 days booster immunization, and serum specific antibodies levels of IgG and $IgG_{2a}$ were determined by enzyme-linked immunosorbent assay. As shown in FIGS. 7A-7B, the control group was injected with the same amount of normal saline, the RBD group was injected with the same amount of antigen without materials, and the S-CpG group as control was injected with single free CpG adjuvant. The result shows that the combination adjuvant groups can activate higher levels of IgG and $IgG_{2a}$ antibody titers, and 5'-CpG-free group has better immune effect, indicating that the combination adjuvants produce more effective synergistic effect.

Figure 8A:
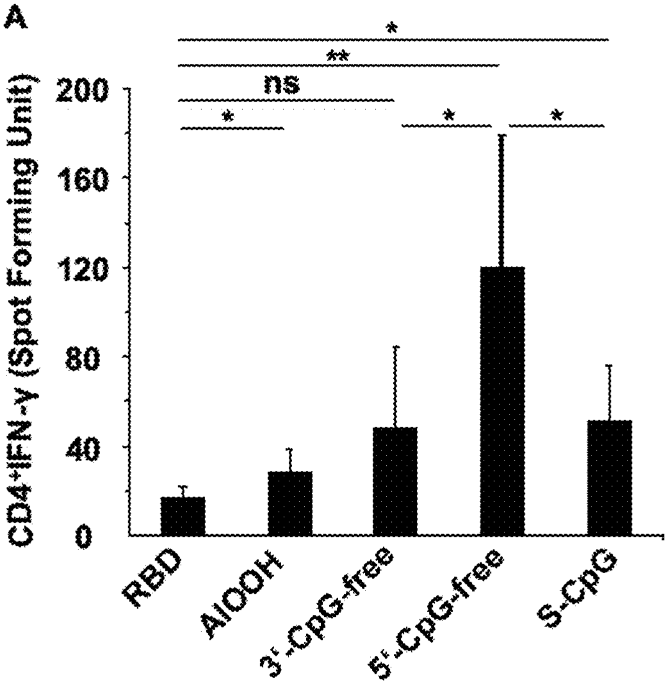
FIGS. 8A-8B show the activation effect of aluminum oxyhydroxide nanorods on $CD4^{+}T$ cells before and after carboxylation and combination.
Figure 8B:
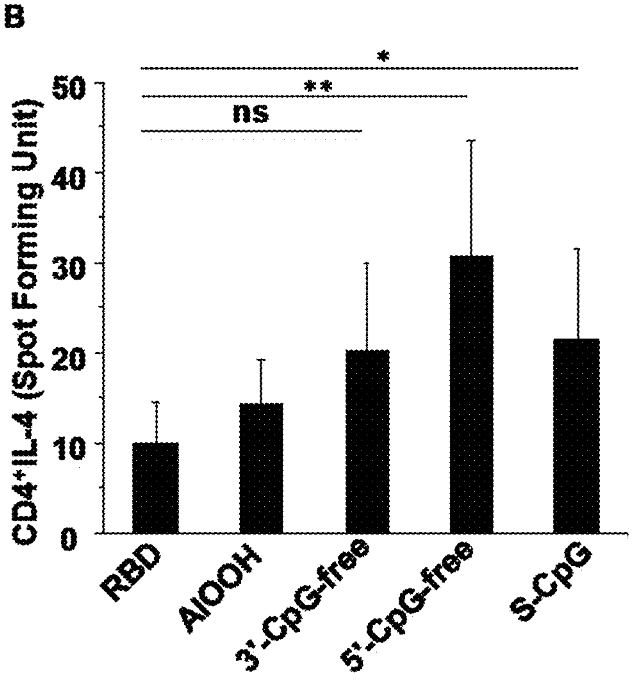
Figure 9:
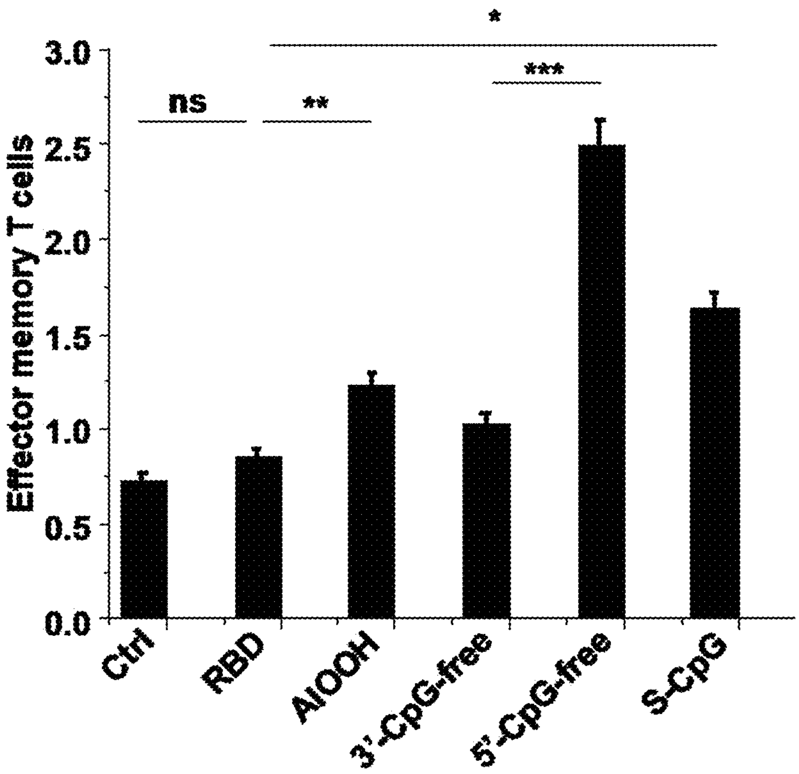
FIG. 9 shows the effect of aluminum oxyhydroxide nanorods on activation of memory T cell before and after carboxylation and combination.

The collected spleen was ground, and one third of the ground cells were screened by CD 4 negative selection kit (Stemcell) to obtain $CD4^{+}T$ cells. Using ELISpot method, the obtained $CD4^{+}T$ cells were stimulated with 5 g/mL of RBD antigen for 36 hours to obtain the cell spots secreting IL-4 and IFN-γ. As shown in FIGS. 8A-8B, FIG. 8A is the statistics of cell spots secreting IFN-γ and FIG. 8B is the statistics of cells secreting IL-4. It can be seen from FIGS. 8A-8B that the combination adjuvants can improve the cellular immune effect, and 5'-Cpg-free group has the better stimulating effect. Another one third of the ground cells were stimulated with 5 μg/mL of RBD antigen for 72 hours, the cells memory level was detected by flow cytometry with the same group setting as above, and the results are shown as FIG. 9. The results further verify the combination adjuvant of 5'-CpG-free has superior immune effect.

Embodiment 7

This embodiment provides an implementation for evaluating the activation of $CD8^+T$ cells and CTL in vivo long-acting immunity of vaccine adjuvants.

Figure 10:
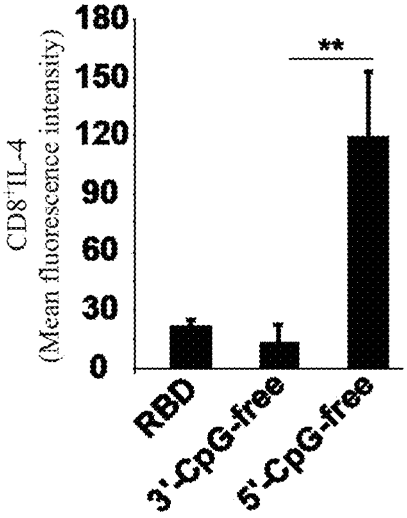
FIG. 10 shows a comparison of cellular immune activation effects of the combination adjuvants on $CD8^{+}T$ cells.
Figure 11:
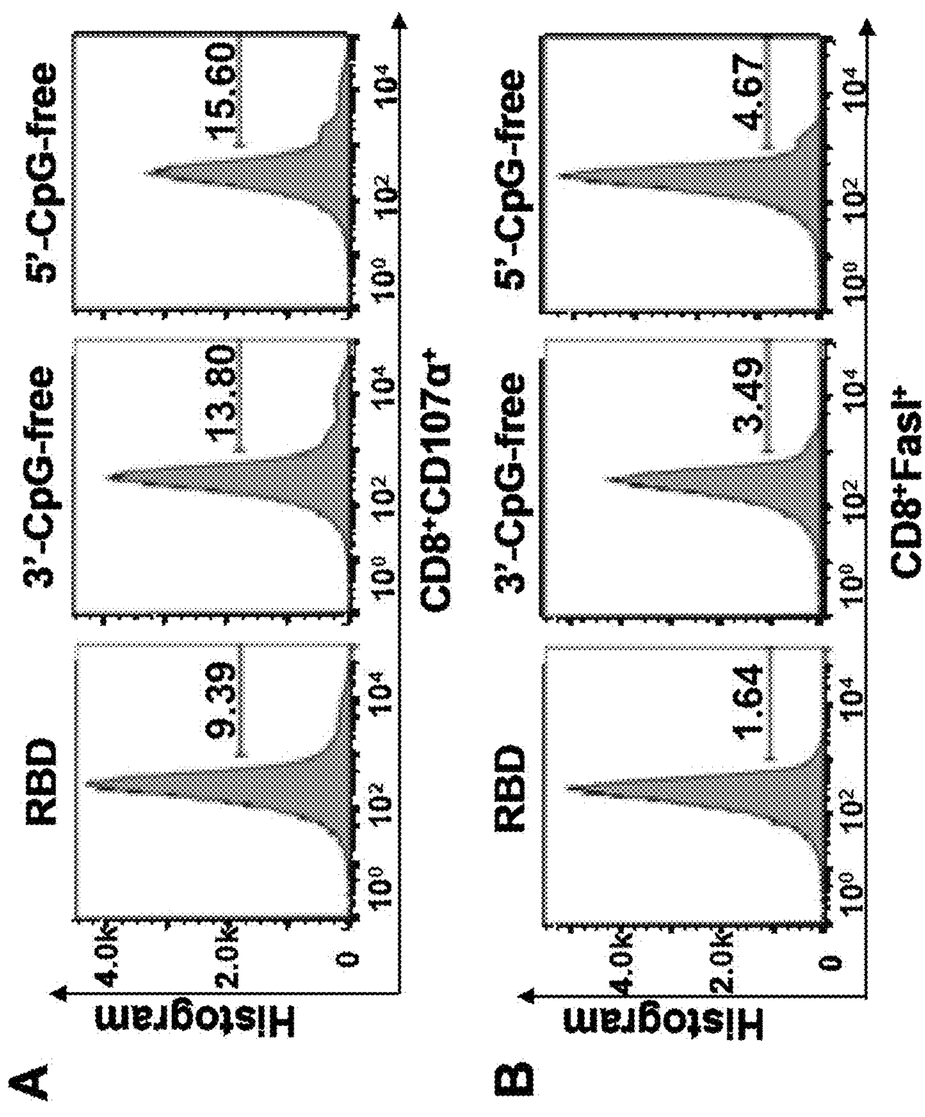
FIG. 11 shows a comparison of CTL activation effects of the combination adjuvants on $CD8^{+}T$ cells (A and B are respectively the expression levels of CD107α and FasL which are the major killing mediums of CTL).

The adjuvants of 3'-CpG-free and 5'-CpG-free obtained in Embodiment 2 were respectively prepared to 5 mg/mL solution, and respectively adsorbed with 40 μg/mL of novel coronavirus RBD antigens. The prepared solution was intramuscularly injected into mouse in a dose of 50 μL per mouse, and the mouse was subjected to first immunization and booster immunization respectively according to the immunization procedure of Day 0 and Day 21. Spleen of the mouse was collected after 7 days booster immunization. The collected spleen was ground, and one third of the ground cells were screened to obtain $CD8^+T$ cells by CD negative selection kit (Stemcell). By using ELISpot method, half of the $CD8^+T$ cells were stimulated with 5 μg/mL of RBD antigen again for 36 hours to obtain the cell spots secreting IL-4. The results of the cell spot statistics are shown in FIG. 10, in which the RBD group as control was injected with the same amount of antigen without adsorbing adjuvant. The results show that the combination adjuvant of 5'-Cpg-free significantly enhances the $CD8^+T$ cell proliferation of secreting IL-4. The remaining half of $CD8^+T$ cells were stimulated with 5 μg/mL of RBD antigen for 72 hours, and the expression of CTL killing mediums was detected by flow cytometry with the same group setting as above, and the results are shown as FIG. 11. It can be found that 5'-CpG-free group can stimulate higher levels of expressions of CTL killing mediums of CD178 and CD107α on the surface of $CD8^+T$ cells, which further verify that the 5'-CpG-free can better stimulate the immune effect.

For any skilled person familiar with the art, without departing from the scope of the technical solution of the present disclosure, the technical content disclosed above can be used to make many possible changes and modifications to the technical solution of the present disclosure or modifications to be equivalent embodiments of equivalent changes. Therefore, any simple modifications, equivalent changes and modifications made to the above embodiments in accordance with the technical essence of the present disclosure without departing from the content of the technical solution of the present disclosure shall still fall within the scope of protection of the technical solution of the present disclosure.

The invention claimed is:

1. A method for preparing a combination vaccine adjuvant based on carboxyl modified aluminum oxyhydroxide nanoparticles, comprising following steps of:

S1. dispersing aluminum oxyhydroxide nanoparticles in deionized water or ethanol to obtain a hydroxy aluminum nanoparticle suspension, adding a silane coupling agent having carboxyl groups or anhydrides for reaction with stirring to obtain carboxylated aluminum oxyhydroxide nanoparticles; and S2. dispersing the carboxylated aluminum oxyhydroxide nanoparticles in a buffer to obtain a carboxylated aluminum oxyhydroxide nanoparticle suspension, adding 1-(3-dimethyl aminopropyl)-3-ethylcarbodiimide hydrochloride and N-hydroxysulfosuccinimide to mix and conduct an activation reaction under a condition of stirring to obtain carboxyl-activated aluminum oxyhydroxide nanoparticles, and then adding amino-terminated CpG to react to obtain a combination vaccine adjuvant, whereby the combination vaccine adjuvant thus prepared shows synergistic effects with antigen in immune responses.

2. The method for preparing a combination vaccine adjuvant based on carboxyl modified aluminum oxyhydroxide nanoparticles according to claim 1, wherein the aluminum oxy hydroxide nanoparticles are aluminum nanoparticles having hydroxyl groups on surface or hydroxyl modified aluminum nanoparticles; the silane coupling agent having carboxyl groups or anhydrides is 3-(triethoxylmethylsilyl) propylsuccinic anhydride.

3. The method for preparing a combination vaccine adjuvant based on carboxyl modified aluminum oxyhydroxide nanoparticles according to claim 1, wherein in step S1, a concentration of the aluminum oxyhydroxide nanoparticle suspension is 0.1 to 20 mg/mL, and a volume ratio of the silane coupling agent to the aluminum oxyhydroxide nanoparticle suspension is 0.01 to 1:100.

4. The method for preparing a combination vaccine adjuvant based on carboxyl modified aluminum oxyhydroxide nanoparticles according to claim 1, wherein in step S1, the conditions of the reaction with stirring are of firstly reacting with stirring at 25 to 35° C. for 30 to 60 minutes, and then reacting with stirring at 100 to 150° C. for 60 to 200 minutes.

5. The method for preparing a combination vaccine adjuvant based on carboxyl modified aluminum oxyhydroxide nanoparticles according to claim 1, wherein in step S2, a concentration of 1-(3-dimethyl aminopropyl)-3-ethylcarbodiimide hydrochloride and N-hydroxysulfosuccinimide is greater than or equal to 100 M, a concentration of the carboxylated aluminum oxyhydroxide nanoparticle suspension is 0.1 to 20 mg/mL, a mass ratio of the carboxylated aluminum nanoparticles to CpG is 5 to 100:1; and in step S2, pH of the buffer is less than or equal to 7.0; and in step S2, the carboxyl-activated aluminum oxyhydroxide nanoparticles react with 5' end or 3' end of amino-terminated CpG sequence to obtain a combination vaccine adjuvant having 3'-CpG-free or 5'-CpG-free.

6. The method for preparing a combination vaccine adjuvant based on carboxyl modified aluminum oxyhydroxide nanoparticles according to claim 1, wherein in step S2, a stirring rotate speed of the activation reaction is 500 to 1000 rpm, an activation time is 20 to 40 minutes, and the activation reaction is carried out at room temperature.

7. The method for preparing a combination vaccine adjuvant based on carboxyl modified aluminum oxyhydroxide nanoparticles according to claim 1, wherein in step S2, a reaction temperature is 25 to 37° C., and a reaction time is 2.5 to 5 hours.

8. A combination vaccine adjuvant prepared by the method of claim 1.

9. An application of the combination vaccine adjuvant of claim 8 in vaccine production.

10. The application according to claim 9, wherein the vaccine is a subunit vaccine or an inactivated vaccine; and the vaccine preparation is used for intramuscular injection.

* * * * *